United States Patent [19]

Borredon

[11] 3,987,173

[45] Oct. 19, 1976

[54] PHARMACEUTICAL PREPARATIONS COMPRISING VINCAMINE ALKALOIDS AND DIHYDROERGOCRISTINE

[75] Inventor: Philippe Borredon, Paris, France

[73] Assignee: Lever Brothers Company, New York, N.Y.

[22] Filed: Feb. 3, 1975

[21] Appl. No.: 546,444

[30] Foreign Application Priority Data

Feb. 4, 1974  United Kingdom................. 5068/74

[52] U.S. Cl................................. 424/261; 424/258
[51] Int. Cl.² .................. A61K 31/47; A61K 31/48
[58] Field of Search............................. 424/261, 258

[56] References Cited
FOREIGN PATENTS OR APPLICATIONS
2,108,993    5/1972    France

OTHER PUBLICATIONS

Louisette et al. — Chem. Abst. vol. 76 (1972) p. 27948w.

Aurousseau et al. — Chem. Abst. vol. 77 (1972) p. 135767r.

Rondeaux et al. — Chem. Abst. vol. 78 (1973) p. 66979t.

*Primary Examiner*—Sam Rosen
*Attorney, Agent, or Firm*—Kenneth F. Dusyn; James J. Farrell; Melvin H. Kurtz

[57] ABSTRACT

The present invention provides certain mixtures of vincamine and ergot alkaloids, in particular their dihydro derivatives and the like, such as e.g. 9,10-dihydroergocristine and vincamine, which show a surprising beneficial combination of pharmacological properties in particular in blood circulation disorders.

The novel mixture of vincamine and an ergot alkaloid, preferably a dihydro ergot alkaloid contains these alkaloids generally in relative weight ratios of 10:1 to 40:1 (calculated as free bases).

3 Claims, No Drawings

PHARMACEUTICAL PREPARATIONS COMPRISING VINCAMINE ALKALOIDS AND DIHYDROERGOCRISTINE

BACKGROUND OF THE INVENTION

Several alkaloids obtainable from ergot (Clairups purpurea) such as ergocristine, to the unspecified stereoisomers of which the systematic name Ergoline - 8β-carboxamide, has been attributed, and dihydro derivatives therefrom are also known in the art and have been investigated as to their pharmacological properties. The dihydro derivatives, such as 9, 10-dihydroergocristine, appear to be pharmacologically very active and show properties such as central vasodilation, anti-adrenalin action and to affect the heart and central nervous system. It has been suggested that these properties include cerebral vasodilation or vasoconstrictor dependent on dosage and decrease in oxygen demand. Experimental work showed that the amounts of blood flowing through the arteries to the brains through the carotid arteries (arteriae carotes) and through the vertebral arteries (arteriae ventrales) are slightly diminishing, whereas the blood pressure of the maxillary veins (venae maxillares) initially decreases superficially, which is followed by an increase. Respiration was hardly affected.

Vincamine, an alkaloid obtainable from periwinkle (Vinca Minor L), to the unspecified stereoisomers of which the systematic name 1H-Indolo [3,2,1-de] pyrido[3,2,1 -ij] [1,5] naphthyridine - 12 - carboxylic acid has been attributed and derivatives thereof as e.g. vincamone to which the name 13α-ethyl-2,3,6,13,13a,13b-hexhydro-1H-indolo [3,2,1-de] pyrido [3,2,1-ij] [1,5] naphthyridin-12 (5H)-one has been attributed, and their salts are also known in the art and several pharmacological properties have been reported.

The above compounds are referred to below as vincamines or a vincamine. A cardiovascular action and cerebral vasodilation increasing cerebral blood circulation have been reported. Experimental work showed that the compound has a slight initial hypotensive effect on the arteries which is followed by a very slight hypertensive action. The flow of blood through the arteries is hardly affected but a tendency towards increase might be noticed. However, the flow of blood returning from the brains via the veins is increased, indicating an increased blood irrigation of the brains.

SUMMARY OF THE INVENTION

It has now been found that certain mixtures of vincamine and ergot alkaloids, in particular their dihydro derivatives and the like, such as e.g. 9,10-dihydroergocristine and vincamine show a surprising beneficial combination of pharmacological properties, in particular in blood circulation disorders.

The novel mixture of vincamine and an ergot alkaloid, preferably a dihydro ergot alkaloid contains these alkaloids generally in relative weight ratios of 10:1 to 40:1 (calculated as free bases) although more ergot alkaloid or its dihydro compound may be present, especially if the relative pharmacological activity of the ergot compound is relatively low.

DETAILED DESCRIPTION

The invention is directed to certain mixtures of at least one ergot-type alkaloid, such as ergocornine, ergocristine and ergocryptine, in particular a dihydro derivative thereof, such as 9,10-dihydroergocristine or its methanesulphonate and vincamine or equivalents thereof such as vincamone, pharmaceutically acceptable salts such as the hydrochloric acid addition salts, tartrate or malate of the above compounds which show valuable pharmacological properties.

The weight ratio of vincamine and ergot alkaloids generally ranges from 10:1 to 40:1 in the case of dihydro (ergot) alkaloids ratios of 15:1 to 25:1 are preferably employed in particular ratios of about 20:1.

The mixture of the two alkaloids according to the invention is preferably applied orally or by intravenous injection of an aqueous solution and the invention thus provides combinations of two alkaloids in particular in unit dosages.

The amount supplied depends on the desired effect, but generally daily doses range from 20–100, preferably 40–80 mg of the alkaloid mixture.

Dependent on the level of dosage and the relative weight ratios of both alkaloids present a combination of the following effects is obtainable: increase of blood pressure in the aorta and the internal carotid arteries (arteriae carotes internae); no appreciable change in the flow of blood through the vertebral arteries (arteriae ventrales), a significant and lasting increase in the flow of blood through the internal carotid arteries, a significant and lasting increase in the flow of blood returning from the brains via the maxillary veins (venae maxillares), a slight decrease in respiration. Summarizing, primarily a selective significant lasting increase in blood circulation in the brains is noted, which increase in blood circulation is appreciably higher than could be anticipated on the basis of the pharmacological properties of the ergot alkaloid and vincamine alone.

The secondary pharmacological effects, such as psychopharmacological effects tested with mice, general effect on blood pressure tested on the femoral artery (arteria femoralis) tested with dogs, were only slight. Apart from the increase of blood circulation in the brain a peripheral increase in blood circulation was noted and no acute or chronic toxic effects noted in the vital organs of rats and mice when the combination was applied orally or parenterally.

The ability of the combination of ergot alkaloids, their dihydro derivatives, in particular 9,10-dihydroergocristine in combination with vincamine or equivalents thereof to increase the blood circulation in the brains and improve oxygen supply without major adverse side-effects is highly significant for the treatment of cerebral circulation disorders, in particular in geriatry. The invention also provides a process for treating cerebral circulation disorders in particular in warm blooded animals in particular humans comprising applying an admixture of a vincamine and an ergot type alkaloid in relative ratios of 10:1 to 40:1.

The invention accordingly provides pharmaceutical compositions and methods for the preparation thereof, which compositions comprise an ergot alkaloid or a dihydro derivative such as 9,10-dihydroergocristine together with vincamine or vincamone and an inert pharmaceutically acceptable carrier. The carrier can be a solid or liquid in which the alkaloid is dissolved, dispersed or suspended. The compositions are preferably in unit dosage form and can take the form of tablets, powders, capsules, solutions, emulsions and liquid suspensions, especially in forms suitable for oral application and injection.

The invention is illustrated by the following example.

EXAMPLE I

The following compounds are dissolved in water and the solution is made up to a volume of 1000 ml at room temperature:
0.50 g dihydroergocristine methanesulphonate
10.00 g vincamine
15.00 g tartaric acid
9.50 g sodium bicarbonate
300.00 g propylene glycol which solution showed a pH of about 4.

In a similar way two solutions were prepared from which in one case the dihydroergocristine and in the other the vincamine was omitted. These solutions, solution A, B and C, are used in making pharmacological comparisons between the effects of the single alkaloid compounds and of the mixture thereof. The effect was tested on groups of dogs, usually consisting of five dogs, mainly using the technique described by Eyraud in Journal de Pharmacologie (Paris) 1970, I 3, 323–338. The dogs were anaesthetized and the above-mentioned solutions containing vincamine, dihydroergocristine and the combination of both at levels of 2.5 mg/kg and 0.125mg/kg respectively, were applied by intravenous injection.

After stabilization of the animal, the following parameters at different time intervals, from half a brain were recorded.

A. Blood pressure of the internal carotid artery (arteria carotis interna) which is a measure for the resistance of the blood vessels at the basis of the brain.
B. The flow of blood through the vertebral artery (arteria ventralis).
C. The flow of blood through the internal carotid artery (arteria carotis interna).
D. The blood pressure in the maxillary vein (vena maxillaris).

The average results at various time intervals after application are tabulated below.

Table I

PHARMACOLOGICAL ACTION OF DIHYDROERGOCRISTINE + VINCAMINE
(Solution A)

|  | 30'' | 1' | 2' | 5' | 10' | 15' | 20' | 25' | 30' |
|---|---|---|---|---|---|---|---|---|---|
| Pressure Internal Carotid Artery (in mm Hg) | 0 | +18 | +30 | +27 | +19 | +13 | + 9 | + 7 | + 8 |
| Flow Vertebral Artery (m$^1$/min) | 0 | − 8 | − 8 | −11 | − 6 | 0 | − 8 | − 9 | 12 |
| Flow Internal Carotid Artery (m$^1$/min) | −14 | 0 | +11 | +44 | +38 | +25 | +26 | +28 | +28 |
| Pressure Maxillary Vein (in mm Hg) | − 6 | 0 | +29 | +49 | +39 | +31 | +23 | + 5 | + 7 |

Table II

PHARMACOLOGICAL ACTION OF VINCAMINE
(Solution B)

|  | 30'' | 1' | 2' | 5' | 10' | 15' | 20' | 25' | 30' |
|---|---|---|---|---|---|---|---|---|---|
| Pressure Internal Carotid Artery (mm Hg) | −19 | 67 | − 8 | + 8 | + 5 | + 4 | + 7 | + 6 |  |
| Flow Vertebral Artery (m$^1$/min) | + 4 | 0 | + 1 | + 2 | + 1 | + 1 | + 3 | + 8 |  |
| Flow Internal Carotid Artery (m$^1$/min) | +10 | + 7 | + 3 | − 3 | + 1 | 0 | + 2 | 0 |  |
| Pressure Maxillary Vein (mm Hg) | +57 | +59 | +79 | +47 | +46 | +54 | +130 | +280 |  |

Table III

PHARAMCOLOGICAL ACTION OF 9,10 — DIHYDROEROGOCRISTINE
(Solution C)

|  | 30'' | 1' | 2' | 5' | 10' | 15' | 20' | 25' | 30' |
|---|---|---|---|---|---|---|---|---|---|
| Pressure Internal Carotid Artery (mm Hg) | + 9 | +16 | +21 | +25 | +27 | +22 | +20 | +17 | +14 |
| Flow Vertebral Artery (m$^1$/min) | −22 | −29 | −26 | −26 | −33 | −35 | −39 | −42 | −46 |
| Flow Internal Carotid Artery (m$^1$/min) | 0 | 0 | 0 | −29 | −33 | −33 | −37 | −41 | −51 |
| Pressure Maxillary Vein (mm Hg) | −14 | −11 | 0 | +17 | +26 | +27 | +26 | +14 | +10 |

From the Tables above it is apparent that the blood circulation in the brain is considerably increased upon application of the two alkaloids in combination without serious adverse side effects and that this effect could not be anticipated on the basis of the action of either alkaloid alone.

What we claim is:

1. A pharmaceutical preparation comprising effective amounts vincamine alkaloid and dihydroergocristine in a weight ratio of 15:1 to 25:1 calculated as free bases.

2. A process for treating cerebral circulation disorders in warm blooded animals, comprising applying an effective amount of an alkaloid admixture of vincamine alkaloid and dihydroergocristine in a weight ratio of 15:1 to 25:1 calculated as free bases.

3. The process according to claim 2, in which the applied daily dosage is from 20 to 100 mg of the alkaloid mixture.

* * * * *